(12) United States Patent
Elsheikh et al.

(10) Patent No.: US 8,895,788 B2
(45) Date of Patent: Nov. 25, 2014

(54) PROCESS FOR THE MANUFACTURE OF HYDROFLUOROOLEFINS

(71) Applicant: Arkema Inc., King of Prussia, PA (US)

(72) Inventors: Maher Y. Elsheikh, Wayne, PA (US); Philippe Bonnet, Lyons (FR); John A. Wismer, Washington Crossing, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 14/159,591

(22) Filed: Jan. 21, 2014

(65) Prior Publication Data

US 2014/0316171 A1    Oct. 23, 2014

Related U.S. Application Data

(62) Division of application No. 13/127,615, filed as application No. PCT/US2009/064139 on Nov. 12, 2009, now Pat. No. 8,642,818.

(60) Provisional application No. 61/116,051, filed on Nov. 19, 2008.

(51) Int. Cl.
*C07C 17/20*    (2006.01)

(52) U.S. Cl.
CPC ..................................... *C07C 17/20* (2013.01)
USPC ............ 570/170; 570/151; 570/164; 570/175

(58) Field of Classification Search
None
See application file for complete search history.

(56) References Cited

U.S. PATENT DOCUMENTS

| | | |
|---|---|---|
| 5,616,819 A | 4/1997 | Boyce et al. |
| 5,710,352 A | 1/1998 | Tung |
| 5,811,603 A | 9/1998 | Elsheikh |
| 5,877,359 A | 3/1999 | Elsheikh |
| 5,969,198 A | 10/1999 | Thenappan et al. |
| 6,013,846 A | 1/2000 | Wismer et al. |
| 6,166,274 A | 12/2000 | Chen et al. |
| 6,472,573 B1 | 10/2002 | Yamamoto et al. |
| 6,528,691 B1 | 3/2003 | Elsheikh et al. |
| 6,881,698 B2 | 4/2005 | Bonnet et al. |
| 7,420,094 B2 | 9/2008 | Petrov et al. |
| 7,563,936 B2 | 7/2009 | Wang et al. |
| 8,398,882 B2 | 3/2013 | Rao et al. |
| 8,410,325 B2 | 4/2013 | Sharratt et al. |
| 8,546,623 B2 | 10/2013 | Sharratt et al. |
| 2007/0112228 A1 | 5/2007 | Mukhopadhyay et al. |
| 2007/0197842 A1* | 8/2007 | Mukhopadhyay et al. ... 570/155 |
| 2008/0051610 A1 | 2/2008 | Wang et al. |
| 2008/0103342 A1* | 5/2008 | Wang et al. .................. 570/256 |

FOREIGN PATENT DOCUMENTS

| | | |
|---|---|---|
| GB | 2 329 386 A | 3/1999 |
| WO | WO 2005/108334 A1 | 11/2005 |
| WO | WO 2007/079431 A2 | 7/2007 |

* cited by examiner

*Primary Examiner* — Sudhakar Katakam
(74) *Attorney, Agent, or Firm* — Steven D. Boyd

(57) ABSTRACT

The invention relates to a process for manufacturing 1,1,1,2-tetrafluoropropene (1234yf, $CF_3$—$CF$=$CH_2$) from 1,1,3,3-tetrachlororopropene (1230za, $CCl_2$=$CH$—$CHCl_2$) and/or 1,1,1,3,3-pentachloropropane (240fa, $CCl_3CH_2CHCl_2$). The process comprises a step of isomerization of 1,1,3,3-tetrafluoropropene (1230za) to 1,1,2,3-tetrachloropropene (1230xa) followed by conversion of the 1,1,2,3-tetrachloropropene (1230xa) to 1,1,1,2-tetrafluoropropene (1234yf) via a hydrofluorination process.

10 Claims, 3 Drawing Sheets

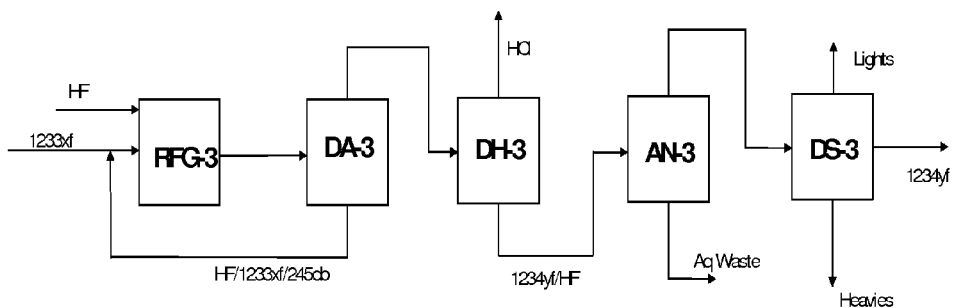
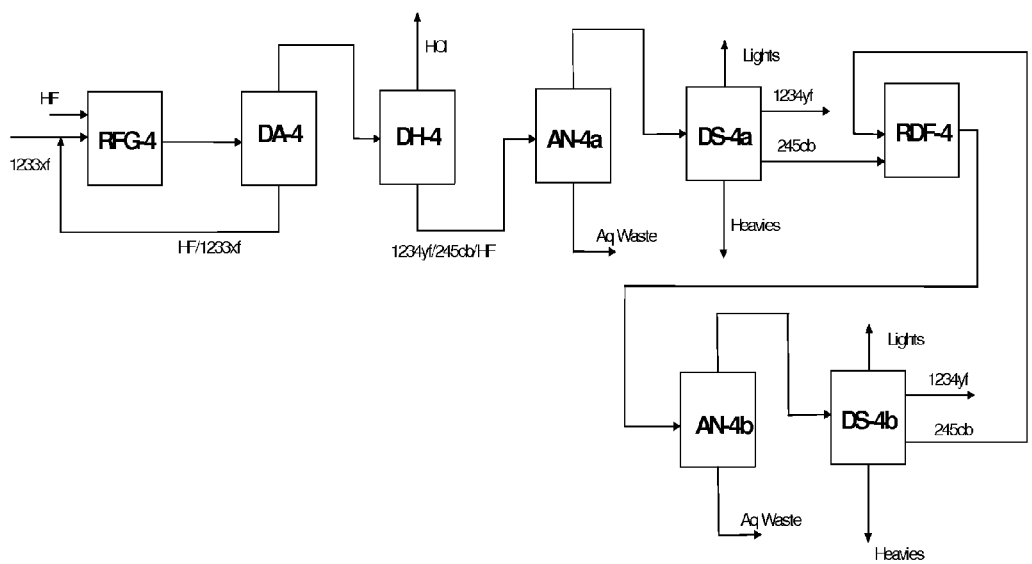

PROCESS FOR THE MANUFACTURE OF HYDROFLUOROOLEFINS

This application is divisional application of U.S. application Ser. No. 13/127,615 filed May 4, 2011 which claims priority to International Application serial Number PCT/US09/64139 filed Nov. 12, 2009, which claims priority to U.S. provisional application Ser. No. 61/116,051 filed Nov. 19, 2008.

FIELD OF THE INVENTION

The present invention relates to a process for the manufacture of hydrofluoroolefins.

BACKGROUND OF THE INVENTION

The Montreal Protocol for the protection of the ozone layer mandates the phase out of the use of chlorofluorocarbons (CFCs). Materials more "friendly" to the ozone layer such as hydrofluorocarbons (HFCs) e.g. 134a replaced chlorofluorocarbons. The latter compounds have proven to be greenhouse gases, causing global warming and could be regulated by the Kyoto Protocol on Climate Change. Replacement materials are needed which are environmentally acceptable i.e. have negligible ozone depletion potential (ODP) and acceptable low global warming potential (GWP). The present invention describes a process for manufacturing of the hydrofluoropropene HFO-1234yf which is useful as a low ODP and low GWP blowing agent for thermoset and thermoplastic foams, solvent, heat transfer fluid or refrigerant such as a mobile air conditioner systems.

US patent publications US2008/0051610 and US2008/0103342 disclose a process that includes a step of the catalytic isomerization of cis 1234ze to trans 1234ze. U.S. Pat. No. 7,420,094 discloses the isomerization of 1234ze to 1234yf with a Cr based catalyst.

SUMMARY OF THE INVENTION

The present invention relates to a process for manufacturing 1,1,1,2-tetrafluoropropene (1234yf, $CF_3-CF=CH_2$) from 1,1,3,3-tetrachlororopropene (1230za, $CCl_2=CH-CHCl_2$) and/or 1,1,1,3,3-pentachloropropane (240fa). The process comprises an isomerization step of 1-chloro-3,3,3-trifluoropropene (1233zd, $CF_3-CH=CHCl$) to 2-chloro-3,3,3 trifluoropropene (1233xf, $CF_3-CCl=CH_2$).

BRIEF SUMMARY OF THE DRAWINGS

FIG. 3 is a schematic of a gas phase fluorination, third step of a process in accordance with the present invention.

FIG. 4 is a schematic of a gas phase fluorination third step followed by a gas phase dehydrofluorination step of a process in accordance with the present invention.

DETAILED DESCRIPTION OF THE INVENTION

Figure 1:
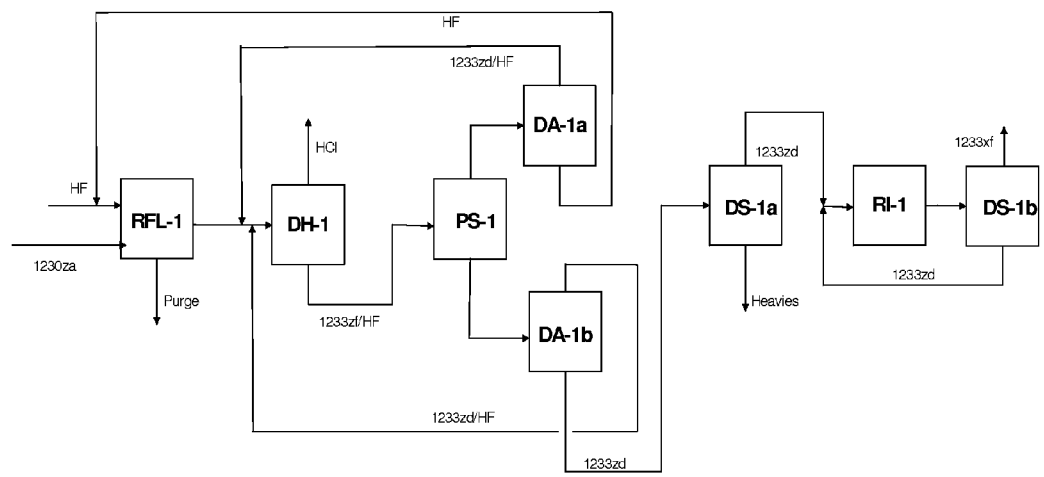
FIG. 1 is a schematic of a liquid phase fluorination first step and isomerization second step of a process in accordance with the present invention.
Figure 2:
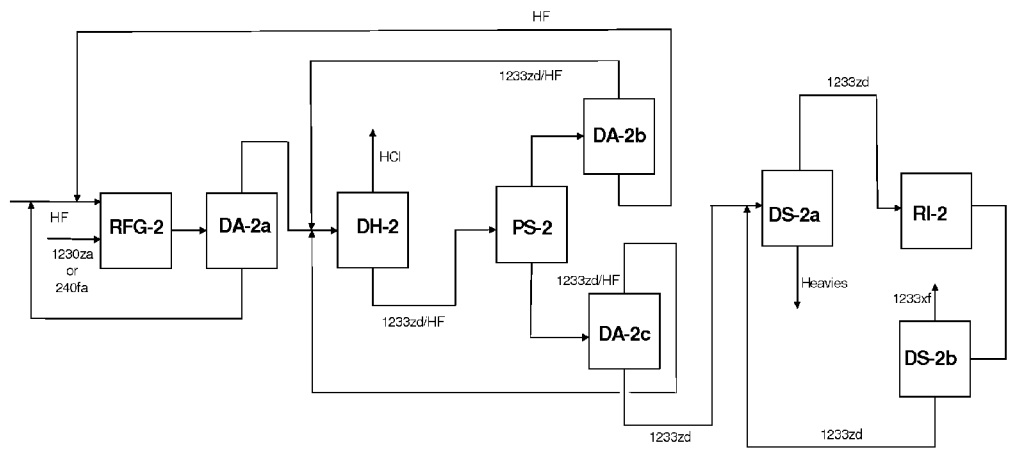
FIG. 2 is schematic of a gas phase fluorination first step and isomerization second step of a process in accordance with the present invention.

The present invention provides a process for producing the hydrofluoroolefin HFO 1234yf from 1230za and/or 240fa. The first step of the process comprises the fluorination of 1230za and/or 240fa to Z/E 1233zd. The first step can be a liquid phase fluorination step as shown in FIG. 1 or a gas phase fluorination step as shown in FIG. 2. A preferred starting material for the liquid phase process is 1230za. In the gas phase process a preferred starting material is 1230za, 240fa or a mixture thereof. The second step of the process of the present invention comprises the isomerization of Z/E 1233zd from the first step to 1233xf. The third step of the process of the present invention comprises the formation of 1234yf via: (a) fluorination of 1233xf to 1234yf; (b) fluorination of 1233xf to 1234yf and 245cb followed by separation of the 245cb for (b1) recycle to the gas phase fluorination reactor or (b2) dehydrofluorination to 1234yf in a separate process; (c) a fluorination of 1233xf to 1234yf and 244bb followed by separation of the 244bb for (c1) recycle to the gas phase fluorination reactor or (c2) dehydrochlorination to 1234yf in a separate process.

An alternative process for producing the hydrofluoroolefin HFO 1234yf from 1230za comprises a step of isomerization of 1,1,3,3-tetrachlororopropene (1230za, $CCl_2=CH-CHCl_2$) to 1,1,2,3-tetrachloropropene (1230xa, $CCl_2=CCl-CH_2Cl$) followed by hydrofluorination either directly to 1234yf or to 2-chloro-3,3,3-trifluoropropene (1233xf, $CF_3-CCl=CH_2$) which is then fluorinated to 1234yf. The conditions of the isomerization step and the fluorination step are as described herein below.

The 1230za used in the first step can be obtained by the reaction of $CCl_4$ and vinyl chloride monomer (VCM, $CH_2=CHCl$) to form 1,1,1,3,3-pentachloropropane (240fa) which can be dehydrochlorinated to produce 1230za.

The present invention is directed towards a process for producing HFO 1234yf from 1230za that comprises the steps of:

a) fluorination of 1,1,3,3-tetrachlororopropene (1230za) and/or 1,1,1,3,3-pentachloropropane (240fa) to Z/E 1-chloro-3,3,3-trifluoropropene (1233zd); followed by b) Isomerization of Z/E 1233zd to 2-chloro-3,3,3-trifluoropropene (1233xf); followed by c) fluorination of 2-chloro-3,3,3-trifluoropropene (1233xf) to 1,1,1,2-tetrafluoropropene (1234yf) directly or in part through coproducts 245cb and/or 244bb.

The first step of the process, fluorination of 1230za and/or 240fa to Z/E 1233zd can be via any process known in the art. For example: the uncatalyzed liquid phase fluorination of 1230za is disclosed in U.S. Pat. No. 5,877,359; the catalyzed gas phase fluorination of 1230za is disclosed in U.S. Pat. No. 5,811,603; U.S. Pat. No. 6,166,274 discloses the fluorination of 1230za to 1233zd in the presence of catalyst such as trifluoroacetic acid or triflic acid. Fluorination catalysts such as $TiCl_4$, $TiF_4$, $SnCl_4$, $SnF_4$, $SbF_5$, $SbCl_5$, $SbF_xCl_y$ (x+y=5), or an ionic liquid are described in U.S. Pat. No. 6,881,698 can also be used. When an Sb(V) type catalyst is used, it is preferred to co-feed low level of $Cl_2$ to maintain the Sb species in an active form.

The second step of the process involves the isomerization of Z/E 1233zd to 1233xf. The isomerization step can be carried out in the gas phase or in liquid phase using respectively a heterogeneous or a homogeneous catalyst. The isomerization step is achievable with a gas phase process in the presence of a heterogeneous catalyst. A suitable heterogeneous catalysts is high surface area $Cr^{(III)}$ catalyst, supported or unsupported, which can optionally contains low levels of one or more co-catalysts selected from cobalt, nickel, zinc or manganese. The level of the co-catalyst, when present, can vary between about 1-5 weight % of the catalyst. The co-catalyst can be incorporated via any known process such as adsorption, mixed powder or co-precipitation. For supported catalyst, the catalyst support can be selected from materials known in the art to be compatible with HF at high temperature and pressure. For example, fluorinated alumina, HF treated activated carbon or carbon graphite are suitable catalyst supports. The catalyst must be activated with HF before use, optionally at pressure above 50 psi.

Suitable heterogeneous catalyst can also be selected from Lewis acids supported catalysts, selected from $Sb^V$, $Ti^{IV}$, $Sn^{IV}$, $Mo^{VI}$, $Nb^V$ and $Ta^V$. Supported antimony halides such as $SbF_5$ are described in U.S. Pat. No. 6,528,691 and are preferred. Other solid catalysts such as NAFION® type polymer, acidic molecular sieves, zeolites can also be used. For the gas phase process the temperature can be varied between 20-500° C., preferably between 100-400° C., Contact times can vary form 0.5 to 100 seconds. A low level of oxidizing agent such as oxygen or oxygen containing gas such as air or chlorine gas can be used, between 0.01-0.1 volume percent to prolong the lifetime of the catalyst.

The isomerization step is also achievable in a liquid phase process in the presence of a homogenous catalyst preferably selected from compounds of group 3, 4, 5, 13, 14 and 15 metal compounds of the Periodic Table of the elements (IUPAC 1988) and their mixtures (groups of the Periodic Table of the elements which were previously called IIIA, IVa, IVb, Va, Vb and VIb). The compounds of the metals are intended to include the hydroxides, oxides and the organic or inorganic salts of these metals, as well as mixtures thereof. Preferred are compounds of aluminium, titanium, tantalum, molybdenum, boron, tin and antimony derivatives. In the process according to the invention the preferred derivatives of the metals are the salts and these are preferably chosen from the halides and more particularly from chlorides, fluorides and chlorofluorides such as $AlF_3$, $TiF_4$, $TaF_5$, $NbF_5$, $MoF_6$, $SnF_4$, $SbF_5$, $SbF_xCl_y$ (x+y)=5. The catalyst must be subjected to activation (by HF or any molecule able to exchange for fluorine) prior to the isomerization step. In the case of antimony type catalyst, a low level of chlorine gas as oxidizing agent can be used to maintain the antimony catalyst in the pentavalent oxidation state. In addition to the above mentioned Lewis acids catalyst, an ionic liquid derived from antimony, titanium, niobium and tantalum is suitable for liquid phase fluorination processes. A description of the preparation of such catalysts is disclosed in U.S. Pat. No. 6,881,698.

The homogenous catalyst for a liquid phase process can also be selected from the Bronsted type family of acids such as $H_2SO_4$, sulfonic type acids such as $ClSO_3H$, $FSO_3H$ or $CF_3SO_3H$ and $CH_3SO_3H$. For the liquid phase process, the operating temperature can be varied between 20-200° C., with a contact time between 0.5-50 hours.

The third step of the process of the present invention comprises the fluorination of 1233xf to 1234yf directly or in whole or in part through coproducts 244bb and/or 245cb. The selectivity of the product obtained will depend on the nature of the catalyst and the processing conditions. The preferred catalyst is a high surface area fluorination catalyst such as $Cr_2O_3$ activated at high pressure with HF, supported or unsupported, and optionally containing about 1-10 weight % of a co-catalyst selected from Ni, Co, Zn or Mn. The catalyst support can be selected from fluorinated alumina, fluorinated chromia, HF treated activated carbon or graphite carbon The process temperature can range from about 20° to 410° C., the molar ratio (MR) of HF/1230xa can range between 4-50, and operating pressure can be from atmospheric to 400 psig. When the operating temperature is about 350°-370°, the molar ratio of HF/1233xf is about 10/1 and the pressure is about 350 psig. The selectivity of the product obtained will favor the formation of 245cb and the olefin 1234yf. The coproducts 1,1,1,2,2-pentafluoropropane (245cb) or 2-chloro-1,1,1,2-tetrafluoropropane (244bb) can be either separated from 1234yf and recycled to the same gas phase fluorination reactor or sent to another part of the process where it can be dehydrofluorinated or dehydrochlorinated respectively to 1234yf by any mean known in the art such as by catalytic dehydrofluorination with a Cr base catalyst or dehydrochlorination utilizing a solid catalyst such as a nickel based catalyst or a salt or alloy thereof. When a supported Lewis acid catalyst is used, it is possible to control the level of fluorination so as to produce 2-chloro-1,1,1,2-tetrafluoropropane (244bb) from the addition of only one mole of HF to one mole of 1233xf. The production of 244b is most convenient at lower operating temperatures, between 20-150° C. The 2-chloro-1,1,1,2-tetrafluoropropane (244bb) can be dehydrochlorinated to 1234yf via a separate catalyzed step utilizing a solid catalyst such as a nickel based catalyst or a salt or alloy thereof. It is also possible to utilize low level of chlorine gas as a free radical initiator in a tube furnace.

The process of the present invention may comprise additional separation steps between each step. The purpose of theses separations could be:
  to remove, totally or partially, any hydracid (HF, HCl) from the flow if required, or
  to isolate a desired product in order to feed it in a subsequent step, or
  to purify a product and removes organic impurities or by products, or
  to dry a product ($H_2O$ removal).

The means used to achieve these additional steps are known in the art and include but are not limited to: distillation, extractive distillation or adsorption.

The process of the present invention is exemplified in the figures, which set forth block flow diagrams of individual or multiple step process in accordance with the present invention. The individual or multistep process in the figures are set out in the form of process modules designed to achieve a specific and arranged in accordance with the process of the present invention. Theses modules comprise:

RFL—comprises a liquid phase fluorination reactor and rectification system comprising an unagitated, jacketed pressure vessel connected to a rectification column. The reactor also acts as the reboiler of the rectification column The HF and organic (1230za) are fed directly to the reactor. The molar feed ratio of HF to organic is dictated by the reaction stoichiometry and the amount of HF leaving the reactor with the rectification column overhead and liquid phase purges. Mixing is provided by the boiling action of the reactor contents. For the most part, the reactor effluent leaves the reactor vessel as a gas and enters the bottom of the rectification column. A small purge from the liquid phase can remove any non-volatiles that may form during the reaction. The rectification column contains either packing or trays designed to provide good mass transfer between up flowing gas and down flowing liquid. The condenser at the top of the column is cooled by either cooling water, chilled water, or some type of refrigeration. The condenser is a partial condenser where the liquid effluent is refluxed directly back to the column. The vapor effluent consists of HCl, HF and organic components.

DH—comprises an HCl distillation system whereby pure HCl is removed from the top of a distillation column. This column can operate between 100 psig and 300 psig. More typically, the HCl is distilled at above 120 psig to allow the use of conventional (−40° C.) refrigeration at the top of the HCl column. The bottoms of this column contains HF and organic with a small residual amount of HCl. The ratio of HF and the organic component in the bottoms is typically close to the azeotropic composition.

PS—comprises a liquid phase separator to separate two liquid phases, one consisting primarily of a hydrochlorofluorocarbon (HCFC) and the other consisting primarily of HF. The HF phase is usually the less dense so that it exits from the top of the phase separator and the HCFC exits as the bottom phase. There is some HF in the HCFC phase and some HCFC in the HF phase. However, the compositions of both phases are far removed from any azeotropic composition. The operating temperature of the phase separator can be between −40° C. and +20° C. However, the lower the temperature, the better the phase separation.

DA—comprises an azeotropic distillation column which distills overhead an azeotropic composition of HF and an organic consisting of one or more HCFC's (hydrochlorofluorocarbons) and HFC's (hydrofluorocarbons). These organic compounds can be either saturated or olefinic. The bottoms composition is either entirely HF or entirely organic, depending on whether the column feed composition is on the HF rich side or the organic rich side of the azeotrope. If the bottoms stream is HF, this stream is normally recycled back to the reactor. If the bottoms stream is organic, it is sent to a conventional distillation train.

DS—comprises a straight distillation, normally done under pressure.

RI—comprises a gas phase isomerization reaction typically done at temperatures above 400° C. in an adiabatic, packed bed reactor. The module consists of a feed vaporizer and superheater. It can include an "economizer", whereby hot effluent is fed to one side and relatively cold reactor feed gases are fed to another side of a heat exchanger. The effluent gases are further cooled before entering a distillation column. Isomerization reactions can be run at varying conversions depending on the equilibrium distribution of isomers. The effluent isomers can have boiling points very close together. However, they typically exhibit close to ideal behavior so can be separated by conventional distillation. As an alternative to the gas phase, this reaction can be done as a homogeneously catalyzed liquid phase reaction. In this configuration, the reactor would be a continuous stirred tank with the effluent being removed as a vapor to effect separation from the catalyst.

RFG—comprises a gas phase fluorination reactor that is an adiabatic packed bed reactor that feeds a gas phase over a solid catalyst. No cooling is needed because the reactor has a low conversion per pass and a high HF feed ratio. The adiabatic exotherm is typically less than 100° C. The feed HF and organic are vaporized in a common vaporizer and superheated to the reactor temperature. This module can also include an "economizer", whereby hot effluent is fed to one side and relatively cold reactor feed gases are fed to another side of a heat exchanger. The effluent gases are further cooled before entering a distillation column.

AN—comprises aqueous absorption, neutralization, drying, compression and liquification. This process module is used to convert a stream containing acid gases that are not economically recoverable into a stream that is acid free and ready for pressure distillation. This module includes an aqueous acid absorber run at atmospheric pressure to absorb HF and possibly HCl from predominantly organic gas streams. The gaseous effluent from the absorber is sent to a neutralizing scrubber that reacts any residual acid with an aqueous base, such as NaOH or KOH. The gaseous effluent from the scrubber is sent to packed beds containing a drying agent such as pellets made of aluminosilicate molecular sieves or calcium sulfate. These dryer beds are typically operated as parallel units so that one can be regenerated while the other is on line. The effluent from the drying bed is sent to a compressor that elevates the pressure of the organic gases to a pressure were they can be easily condensed. The effluent gases from the compressor are then cooled and totally condensed. They can then be pumped as a liquid to any pressure for the purposes of distillation.

RDF—comprises a gas phase dehydrofluorination which is typically done at temperatures exceeding 400° C. and near atmospheric pressure in a furnace type reactor. Heat must be supplied continuously to the reaction zone because the dehydrofluorination is very endothermic. Typically this will be done by sending the process gases through tubes that are heated by the hot gases of a combustion furnace. Heterogeneous catalysts can be used but coking can be a problem at elevated temperatures. An alternative is to use a chlorine initiated free radical reaction. This module can include a feed vaporizer, superheater, and possibly an economizer, a heat exchanger designed to use the hot effluent gases to heat relatively cold feed gases. This reactor typically operates at between 50 and 90% conversion so that the unreacted feed is recovered for recycle downstream.

RDC—comprises a gas phase dehydrochlorination typically done the same way as process module RDF except that the reaction is a dehydrochlorination instead of a dehydrofluorination.

The lower case letter used in the figures is used to distinguish multiple appearances of the same type of module in the same figure.

FIG. 1 is a block flow diagram of a process in accordance with the present invention for converting 1230za to 1233xf using a liquid phase fluorination step. The figure incorporates the modules described above. In FIG. 1, 1230za and HF are fed to reaction module RFL-1. The reaction takes place in a predominantly HF rich medium without a catalyst. HCl and the 1233zd/HF exit the top of the rectification column of RFL-1. The vapor effluent of RFL-1 enters DH-1 to remove HCl as a pure overhead product. The bottoms of DH-1 consist of primarily 1233zf (both E and Z isomers) and HF at a near azeotropic composition. This is fed to module PS-1 to effect a liquid phase separation. The top HF rich phase is sent to module DA-1a, where HF is separated as a bottoms stream for recycle to the reactor. The overhead azeotrope of 1233zd and HF is recycled back to DH-1 to allow any residual HCl and light organics to be stripped out in this column before the azeotrope gets recycled to phase separation. The bottoms stream from PS-1 goes to module DA-1b, which removes a 1233zd stream devoid of HF as a bottoms stream. The overhead from DA-1b is recycled to DH-1 for the same reason that the DA-1a azeotrope was recycled to DH-1. The bottoms of DA-1b are sent to process module DS-1a that separates any heavies from the 1233zd. The overhead from DS-1 is 1233zd and is sent to module RI-1- an isomerization reactor that operates at less than 50% conversion. The effluent from this reactor contains 1233zd. DS-1b represents a distillation train required to separate 1233xf from 1233zd. The higher boiling 1233zd gets recycled to RI-1.

FIG. 2 is a block flow diagram of the first two steps of a process in accordance with the present invention for converting 1230za and/or 240fa to 1233xf using a gas phase fluorination step. 1230za and/or 240fa and HF are fed to reaction module RFG-2. The reaction takes place in a gas phase with a catalyst. The reactor effluent consists of predominantly HCl, 1233zd, unreacted 1230za, and excess HF. The reactor effluent of RFG-2 enters DA-2a to remove HF and unreacted F1230za as a bottoms that is recycled to the reactor. The overhead, which consists predominantly of HCl and the azeotrope of HF and 1233zd (both E and Z isomers), is sent to DH-2, which removes HCl as a pure overhead product. The bottoms of DH-2 consists of primarily 1233zd (both E and Z isomers) and HF at a near azeotropic composition. This is fed to module PS-2 to effect a liquid phase separation. The top HF rich phase is sent to module DA-2b, where HF is separated as a bottoms stream for recycle to the reactor. The overhead azeotrope of 1233zd and HF is recycled back to DH-2 to allow any residual HCl and light organics to be stripped out in this column before the azeotrope gets recycled to phase separation. The bottoms stream from PS-2 goes to module DA-2c, which removes an organic stream devoid of HF as a bottoms stream. The overhead from DA-2c is recycled to DH-2 for the same reason that the DA-2b azeotrope was recycled to DH-2. The bottoms of DA-2c is sent to process module DS-2a that separates any heavies from the 1233zd. The overhead from DS-2a is 1233zd and is sent to module RI-2, an isomerization reactor that operates at less than 50% conversion. The effluent from this reactor contains 1233zd and 1233xf. It is processed in DS-2b, which represents a distillation train to separate 1233xf from 1233zd. The higher boiling 1233zd gets recycled to DS-2a.

FIG. 3 is a block flow diagram of the third step of a process in accordance with the present invention for converting 1233xf to 1234yf in one reaction step. The process modules are as described above. 1233xf and HF are fed together with a recycle stream containing 1233xf, 245cb, and HF into process module RFG-3. The overall HF to 1233xf molar feed ratio, including amounts of both components in the recycle is typically about 5/1. The 1233xf can hydrofluorinate to 1234yf or overhydrofluorinate to 245cb. The tendency of 245cb to dehydrofluorinate to 1234yf in the reactor serves to establish an equilibrium among 1233xf, 1234yf, and 245cb. Once this equilibrium is established, there is no net accumulation of 245cb in the reactor. The conversion of 1233xf to 1234yf is typically 12% for a reaction temperature of 377° C. and an HF molar feed ratio of 5. The mole ratio of 1234yf to 245cb achieved in the reactor is typically slightly less than 2. The effluent from RFG-3 is fed to process module DA-3. The bottoms of this module contains 1233xf, 245cb and HF for recycle to module RFG-3. The overhead from this module contains HCl, HF and 1234yf. The HF and 1234yf are in approximately azeotropic proportions. This steam is fed to process module DH-3, where HCl is distilled overhead as a pure product. The bottoms of DH-3 is fed to AN-3 which removes HF and trace HCl from the organics and provides as an effluent a liquid organic stream that can be distilled under pressure. The process module DS-3 separates 1234yf from any light and heavy impurities.

FIG. 4 sets out a block flow diagram of an alternative third step of a process for converting 1233xf to 1234yf wherein 245cb is an intermediate. The process modules are as described above, In this process the catalyst and process conditions used for the fluorination step are not sufficient to affect dehydrofluorination of 245cb. This occurs when the HF molar feed ratio is in fairly high excess, there is substantial overfluorination to 245cb. This 245cb is dehydrofluorinated separately. 1233xf and HF are fed together with a recycle stream containing 1233xf into process module RFG-4. The overall HF to 1233xf molar feed ratio, including amounts of both components in the recycle is typically about 5/1. The 1233xf can hydrofluorinate to 1234yf or overhydrofluorinate to 245cb. The selectivity to 1234yf is typically about 65%. The reactor effluent is sent to process module DA-4, which removes HF and 1233xf as a bottoms recycle stream that goes back to the reactor RFG-4. The overhead from this module contains HCl, 245cb, 1234yf and HF in an amount determined by the azeotropic composition of HF and the two organic components. This is sent to module DH-4, which removes HCl as an overhead and sends the bottoms containing HF, 1234yf and 245cb to AN-4a. This module removes HF and trace HCl from the organic gases. Note that the presence of 245cb means that there is much more HF present than in the process set out in FIG. 2. It may be feasible to recover anhydrous HF by one of many methods well known to those skilled in the art, such as membrane separation or sulfuric acid absorption. The effluent from AN-4a is sent to process module DS-4a, which separates by distillation 1234yf, 245cb, light impurities, and heavy impurities. The 245cb is fed to process module RDF-4, which dehydrofluorinates 245cb to 1234yf. The effluent is fed to process module AN-4b to remove HF from the organic gases. The effluent from AN-4b is sent to DS-4b, which separates by distillation light impurities, heavy impurities, unreacted 245cb for recycle to RDF-4 and product 1234yf.

Figure 5:
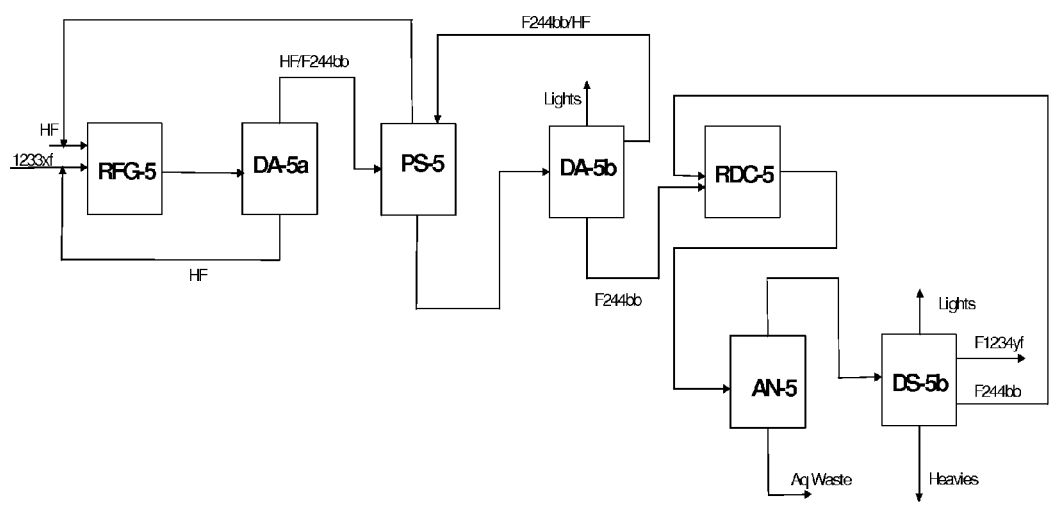
FIG. 5 is a schematic of a gas phase fluorination step followed by a gas phase dehydrochlorination step of a process in accordance with the present invention.

FIG. 5 is a block flow diagram of an alternate third step of a process for converting 1233xf to 1234yf, through intermediate 244bb. The process modules are as described above. HF in high molar excess and 1233xf are fed into process module RFG-5. This reactor operates at moderate temperature (<100° C.) with high conversion and selectivity to 244bb. The effluent is sent to DA-5a which recovers HF in the bottoms for recycle to the reactor. The overhead from DA-5a is HF and 244bb in approximately azeotropic proportions. This stream is sent to process module PS-5, which separates an HF rich upper liquid phase for recycle to the reactor. The organic rich phase is sent to module DA-5b, which recovers the 244bb/HF azeotrope as an overhead liquid for recycle. In order to avoid accumulating lights in the recycle, a vapor phase purge is taken from the overhead steam before it is recycled to PS-5. The 244bb bottoms is sent to process module RDC-5, which partially dehydrochlorinates 244bb to 1234yf. The effluent from RDC-5 is sent to AN-5, which removes HCl from the organic gases. The pumpable liquid effluent from AN-5 is sent to process module DS-5b, which recovers 1234yf product from light impurities, heavy impurities and 244bb, which is recycled to RDC-5- the dehydrochlorination reactor.

What we claim:

1. A process for preparing 1,1,1,2-tetrafluoropropene (1234yf) from 1,1,3,3-tetrachloropropene (1230za) comprising the steps of:
    isomerization of 1,1,3,3-tetrachloropropene (1230za) to 1,1,2,3-tetrachloropropene (1230xa); followed by
    conversion of said 1,1,2,3-tetrachloropropene (1230xa) to 1,1,1,2-tetrafluoropropene (1234yf) via a process comprising hydrofluorination.

2. The process of claim 1 wherein said isomerization is carried out in the liquid phase in the presence of a homogeneous catalyst or in the gas phase in the presence of a heterogeneous catalyst.

3. The process of claim 2 wherein said heterogeneous catalyst is selected from the group consisting of a soluble Lewis acid of $Sb^V$, $Ti^{IV}$, $Sn^{IV}$, $Mo^{VI}$, $Nb^V$ and $Ta^V$; antimony halides; acidic molecular sieves; Cr and zeolites.

4. The process of claim 3 wherein said heterogeneous catalyst is supported or unsupported.

5. The process of claim 3 wherein said heterogeneous catalyst further comprises a co-catalyst selected from the group consisting of cobalt, nickel, zinc and manganese.

6. The process of claim 5 wherein said co-catalyst is present in amounts from about 1 to 5 weight percent of said catalyst.

7. The process of claim 2 wherein said homogenous catalyst is selected from the group consisting of: aluminum, titanium, tantalum, molybdenum, boron, tin, antimony and salts thereof and Bronsted acids.

8. The process of claim 7 wherein said salts are chlorides, fluorides or chlorofluorides.

9. The process of claim 4 wherein said support is selected from the group consisting of fluorinated alumina, fluorinated chromia, Hf treated activated carbon and fluorinated graphite.

10. The process of claim 1 wherein said 1230za is prepared via reaction of $CCl_4$ and vinyl chloride monomer followed by dehydrochlorination.

* * * * *